US00PP19388P2

(12) United States Plant Patent
Burton

(10) Patent No.: US PP19,388 P2
(45) Date of Patent: Oct. 28, 2008

(54) ***GERANIUM* HYBRID PLANT NAMED 'THUNDER CLOUD'**

(50) Latin Name: *Geranium traversii×sessiliflorum*
Varietal Denomination: Thunder Cloud

(76) Inventor: Stephen Burton, 1896 Hamilton Road, Cambridge (NZ)

( * ) Notice: Subject to any disclaimer, the term of this patent is extended or adjusted under 35 U.S.C. 154(b) by 0 days.

(21) Appl. No.: 11/823,592

(22) Filed: Jun. 28, 2007

(51) Int. Cl.
*A01H 5/00* (2006.01)

(52) U.S. Cl. ..... Plt./324

(58) Field of Classification Search ..... Plt./324
See application file for complete search history.

(56) References Cited

U.S. PATENT DOCUMENTS

PP14,701 P2 * 4/2004 Fross ..... Plt./324

OTHER PUBLICATIONS

UPOV ROM GTITM Computer Database, GTI Jouve Retrieval Software 2007/05 Citations for 'Thunder Cloud'.* New Zealand Plant Variety Rights GER017 filed Jan. 16, 2006. Published information from New Zealand PVR site attached.
Plant material first became available to the public on Sep. 20, 2006 as the result of a New Zealand sale.

* cited by examiner

*Primary Examiner*—Wendy C. Haas
(74) *Attorney, Agent, or Firm*—Audrey Charles

(57) ABSTRACT

A new and distinct cultivar of *Geranium* plant named 'Thunder Cloud', characterized by its white-colored flowers having pink-colored venation, dark purple-colored foliage, and rosette growth habit.

1 Drawing Sheet

Latin name of genus and species of plant claimed: *Geranium traversii×sessiliflorum.*
Variety denomination: 'Thunder Cloud'.

BACKGROUND OF THE INVENTION

The present invention relates to a new and distinct cultivar of *Germanium* plant botanically known as *Geranium traversii×sessiliflorum* and hereinafter referred to by the cultivar name 'Thunder Cloud'.

The new cultivar originated in a controlled breeding program in Cambridge, New Zealand throughout 2000 to 2004. The objective of the breeding program was to select for *Geranium* hybrids having darker foliage color.

The new *Geranium* cultivar is the result of open-pollination. The female (seed) parent of the new cultivar is the selection designation *Geranium traversii* 'Nigra', not patented, characterized by its purple-colored foliage, and clumping growth habit. The male (pollen) parent of the new cultivar is the species designated *Geranium sessiliflorum,* not patented, characterized by its green-bronze colored foliage, and clumping growth habit. The new cultivar was discovered and selected as a single flowering plant within the $F_1$ progeny of the above stated open-pollination during November 2002 in a controlled environment at Cambridge, New Zealand.

Asexual reproduction of the new cultivar by terminal stem cuttings since December 2002 at Cambridge has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Thunder Cloud' as a new and distinct cultivar of *Geranium* plant:

1. White-colored flowers having pink-colored venation;
2. Dark purple-colored foliage; and
3. Rosette growth habit.

Plants of the new cultivar differ from plants of the female and male parents primarily in foliage color.

Of the many commercially available *Geranium* cultivars known to the inventor, the most similar in comparison to the new cultivar is 'Purple Passion', U.S. Plant patent application Ser. No. 11/704,787. However, in side by side comparisons, plants of the new cultivar differ from plants of 'Purple Passion' in the following characteristics:

1. Plants of the new cultivar have darker and smaller foliage than plants of 'Purple Passion'; and
2. Plants of the new cultivar have a flower color different from plants of 'Purple Passion'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Thunder Cloud'. The plants were grown in a greenhouse at Cambridge, new Zealand.

DETAILED BOTANICAL DESCRIPTION

Figure 1:
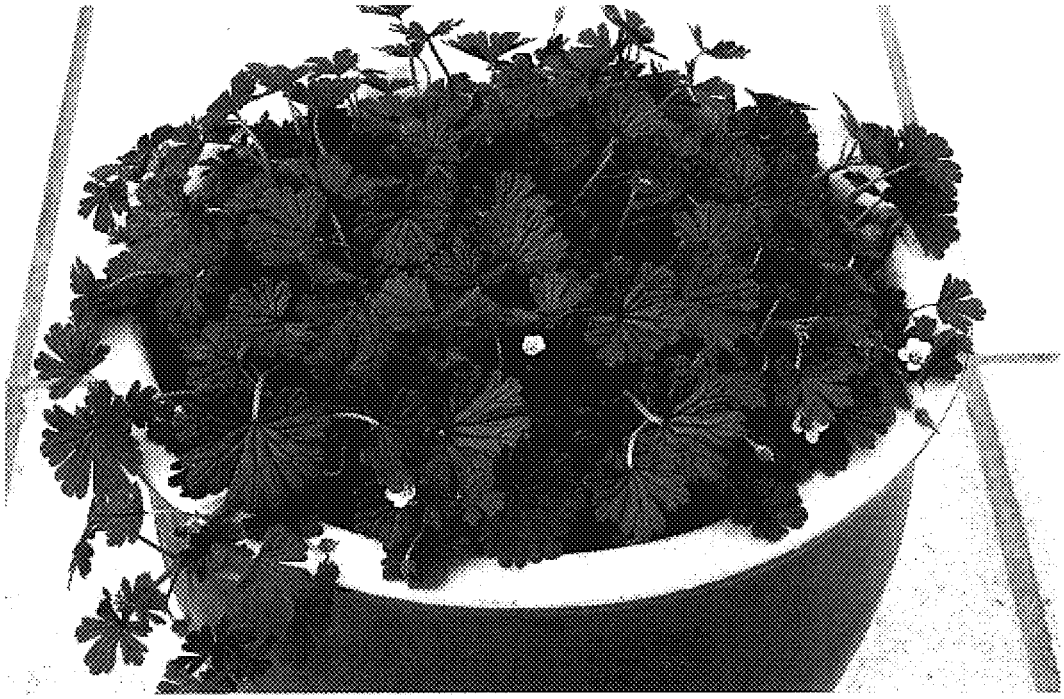
FIG. 1 illustrates the overall growth and flowering habit of 'Thunder Cloud'.
Figure 2:
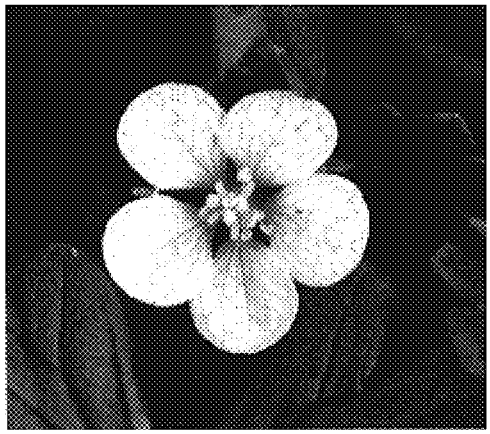
FIG. 2 illustrates a close-up view of an individual flower of 'Thunder Cloud'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Color Chart of The Royal Horticultural Society, London, England, 2001 edition, except where general color terms of ordinary significance are used. The color values were determined on Mar. 20, 2007 between 11:00 a.m. and 1:30 p.m. under natural light conditions in Cambridge, New Zealand.

The following descriptions and measurements describe plants produced from cuttings taken from stock plants and grown in an open greenhouse under conditions comparable to those used in commercial practice. The plants were grown at Cambridge, New Zealand in 12 cm pots for 20 weeks utilizing a soilless growth medium. Greenhouse temperatures were approximately 65° F. to 77° F. (18° C. to 25° C.) during the day and approximately 54° F. to 65° F. to (12° C. to 18° C.) during the night.

Botanical classification: *Geranium traversii×sessiliflorum* cultivar Thunder Cloud Parentage:

*Female parent.*—*Geranium traversii* 'Nigra', not patented.

*Male parent.*—*Geranium sessiliflorum*, not patented.

Propagation:

*Type cutting.*—Stem cutting or tissue culture.

*Time to initiate roots in tissue culture.*—Approximately 2 to 3 weeks.

*Time to produce a rooted stem cutting.*—Approximately 5 to 6 weeks.

*Root description.*—Fine, fibrous.

*Rooting habit.*—Freely branching.

Plant description:

*Crop time.*—Approximately 15 to 20 weeks from tissue culture plantlet to finish in a 12 cm pot.

*Growth habit and general appearance.*—'Thunder Cloud' is a low growing herbaceous perennial having a rosette growth habit with runners. Foliage surrounds the plant producing a symmetrical rounded habit. In full sun, foliage is smaller. In partial shade, larger foliage is produced. In either exposure the symmetrical rounded outline is retained. Low, spreading habit is the result of seasonal runners arising from the center of the plant and spreading in equal distance. These runners appear in spring and die off by winter.

*Size.*—A plant in a 12 cm wide container in full sun measures approximately 13.1 cm tall and approximately 31.1 cm wide, not including runners.

*Branching habit.*—Freely basal branching with short clumping branches close to the soil. Quantity of main branches per plant: Approximately 9.

*Branch.*—Strength: Weak. Length: Approximately 1.6 cm. Diameter. Approximately 6.2 mm. Length of central internode: Approximately 1.3 mm. Texture: Pubescent with soft appressed hairs. Color of young and mature stems: 59D.

*Runner.*—Strength: Weak. Length: Approximately 18.8 cm. Diameter: Approximately 2.6 mm. Length of central internode: Approximately 4.1 cm. Texture: Pubescent with soft appressed hairs. Color of young and mature runners: N199A.

Foliage description:

*General description.*—Quantity of leaves per main branch: Approximately 7. Fragrance: None. Form: simple. Arrangement on flowering stem: Both opposite and alternate.

*Leaves.*—Aspect: Perpendicular to obtuse angle to petiole. Shape: Orbicular; lobed halfway down leaf blade into approximately five to seven segments; each segment further divided with 3 shallow secondary lobes. Margin: Create. Apex: Base: Cordate. Venation pattern: Palmate. Length of mature leaf at center of stem: Approximately 2.7 cm. Width of mature leaf at center of stem: Approximately 5.0 cm. Texture of upper and lower surfaces: Semi-coriaceous and densely pubescent with silvery white appressed hairs having a shiny appearance. Color of upper surface of young and mature foliage N187A with venation of 187B. Color of lower surface of young and mature foliage 197A with venation of 197B.

*Petiole.*—Length: Approximately 11.9 cm. Diameter: Approximately 1.9 mm. Texture: Pubescent with appressed hairs having a shiny appearance. Color: 197A at least attachment transitioning within approximately 1 cm distance to 187B.

*Stipule.*—Apex: Elongated acuminate. Length: Approximately 2 to 5 cm. Diameter: Approximately 5 to 10 mm.

Flowering description:

*Flowering habit.*—'Thunder Cloud' is freely flowering under outdoor growing conditions with substantially continuous blooming from spring through autumn.

*Lastingness of individual bloom on the plant.*—Approximately 5 to 7 days.

Flower description:

*Type.*—Single, occasionally paired, erect, funnel-shaped. Flowers are borne beneath the foliage. Fragrance: None. Quantity per plant: Approximately 12.

*Bud.*—Rate of opening: Generally takes 2 to 3 days for bud to progress from first color to fully open flower. Quantity: Approximately 6.

*Bud just before opening.*—Shape: Oblong, 3 sided. Length: Approximately 6.6 mm. Diameter: Approximately 4.5 mm. Color: N187A.

*Corolla.*—Diameter: Approximately 1.2 cm.

*Petals.*—Quantity: 5. Shape: Broadly spatulate. Margins: Entire, undulate, and recurved. Apex: Rounded. Base: Attenuate. Length: Approximately 8.4 mm. Width: Approximately 5.2 mm. Texture of upper and lower surfaces: Glabrous. Color of upper and lower surfaces when first open: Pure white with venation of 69B. Color of upper and lower surfaces when fully open: Pure white with venation of 69A.

*Calyx.*—Composed of 5 overlapping sepals. Shape: Elliptical prominent apical tip. Length: Approximately 4.0 to 5.0 mm. Width: Approximately 2 to 3 mm.

*Sepals.*—Quantity per flower: 4 to 5, fused at base. Shape: Linear. Apex: Acute. Length: Approximately 6.3 mm. Width: Approximately 4.1 mm. Texture of inner surface: Pubescent with appressed hairs having a shiny appearance. Texture of outer surface: Pubescent with appressed hairs having a dull appearance. Color of inner surface: 1B. Color of outer surface: N66C.

*Peduncle.*—Length: Up to 7.6 cm.

*Reproductive organs.*—Androecium: Stamen quantity: 10, arranged in 2 whorls. Stamen length: Approximately 4.0 mm. Anther shape: Bilobed. Anther length: Approximately 2.0 mm. Anther color: 70D. Pollen amount: Pollen color: 9B. Gynoecium: 5 lobed. Stigma: 5. Stigma color 24B. Ovary diameter: Approximately 4.0 mm. Ovary color: 1B N66C.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Thunder Cloud', substantially as herein shown and described.

* * * * *